United States Patent [19]

Teslawski et al.

[11] Patent Number: 4,517,985
[45] Date of Patent: May 21, 1985

[54] NEONATE ULTRASONIC SCANNER

[75] Inventors: Georg Teslawski, Menlo Park; Paul D. Corl, Mountain View, both of Calif.

[73] Assignee: Diasonics, Inc., Milpitas, Calif.

[21] Appl. No.: 598,492

[22] Filed: Apr. 9, 1984

Related U.S. Application Data

[63] Continuation of Ser. No. 383,562, Jun. 1, 1982, abandoned.

[51] Int. Cl.³ .............................................. A61B 10/00
[52] U.S. Cl. ..................................... 128/660; 73/620
[58] Field of Search ................................ 128/660–663; 73/589, 593, 597, 606, 607, 618–621, 629, 644

[56] References Cited

U.S. PATENT DOCUMENTS

| | | | |
|---|---|---|---|
| 3,990,300 | 11/1976 | Kusoff | 73/621 |
| 4,059,098 | 11/1977 | Murdock | 128/660 |
| 4,130,022 | 12/1978 | Goodrich et al. | 128/660 |
| 4,141,347 | 2/1979 | Green et al. | 128/663 |
| 4,151,834 | 5/1979 | Sato et al. | 128/660 |
| 4,287,767 | 9/1981 | Kretz | 128/660 |
| 4,375,818 | 3/1983 | Suwaki et al. | 128/660 |
| 4,383,447 | 5/1983 | Kretz | 128/660 |
| 4,424,813 | 1/1984 | Havlice et al. | 128/660 |

Primary Examiner—Lee S. Cohen
Assistant Examiner—Steven Falk
Attorney, Agent, or Firm—Blakely, Sokoloff, Taylor & Zafman

[57] ABSTRACT

An ultrasonic scanner for medical diagnostics is disclosed. The scanner includes an upper head assembly and a lower drive assembly. The upper head assembly includes a fluid chamber filled with a liquid acoustic couplant. An oscillating transducer is driven in an asymmetric motion by a linkage coupled off-center to a flywheel within the fluid chamber. An inflatable bladder is provided in the upper assembly which is in fluid communication with the fluid chamber. The application of force to the membrane boot of the scanner forces fluid into the bladder. Once the external pressure is removed, the bladder is biased such that it is compressed, thereby forcing fluid to return to the fluid chamber and maintaining a generally constant pressure within the chamber. Supporting electronics are provided including means for compensating for the asymmetric motion of the transducer.

7 Claims, 12 Drawing Figures

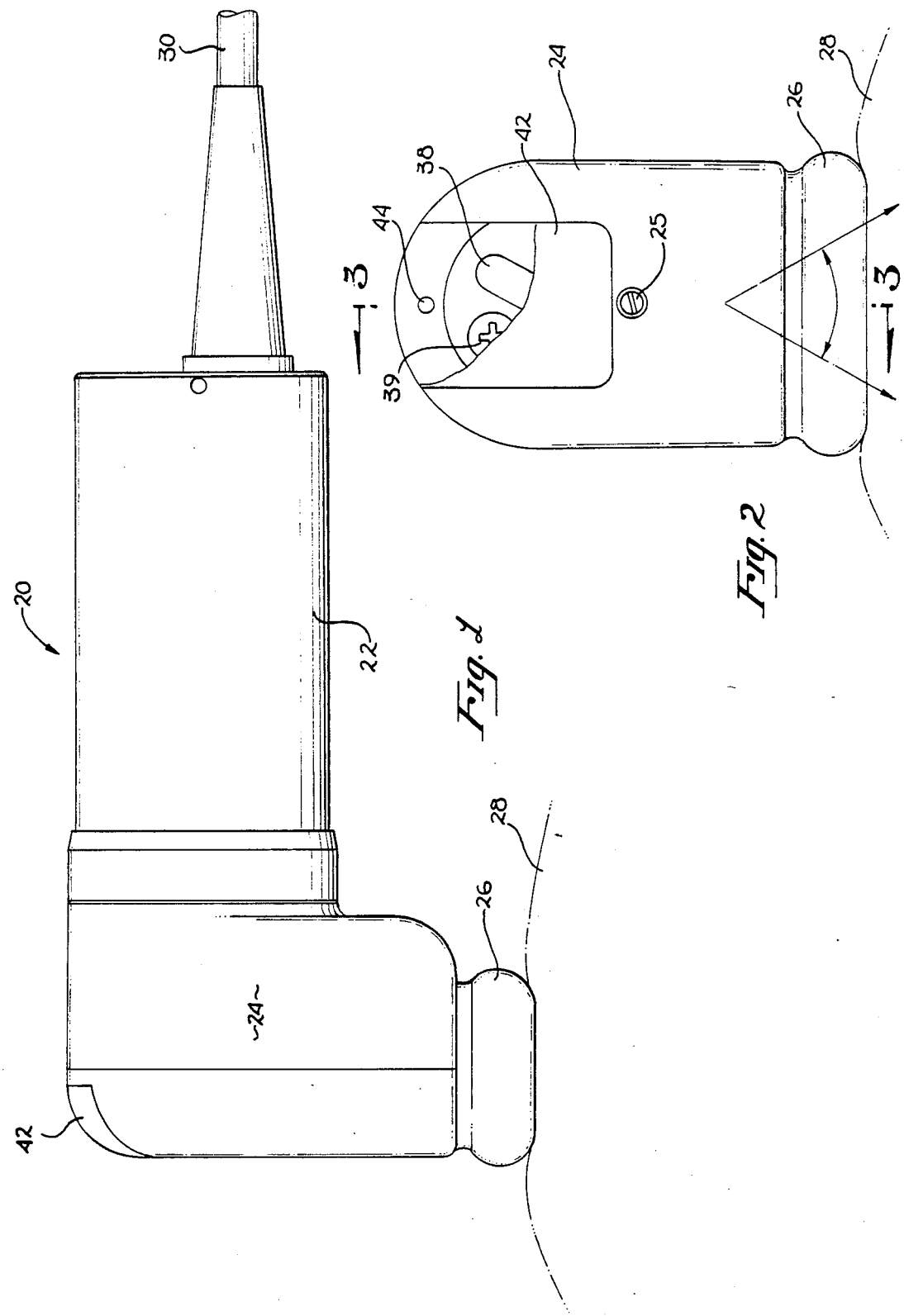

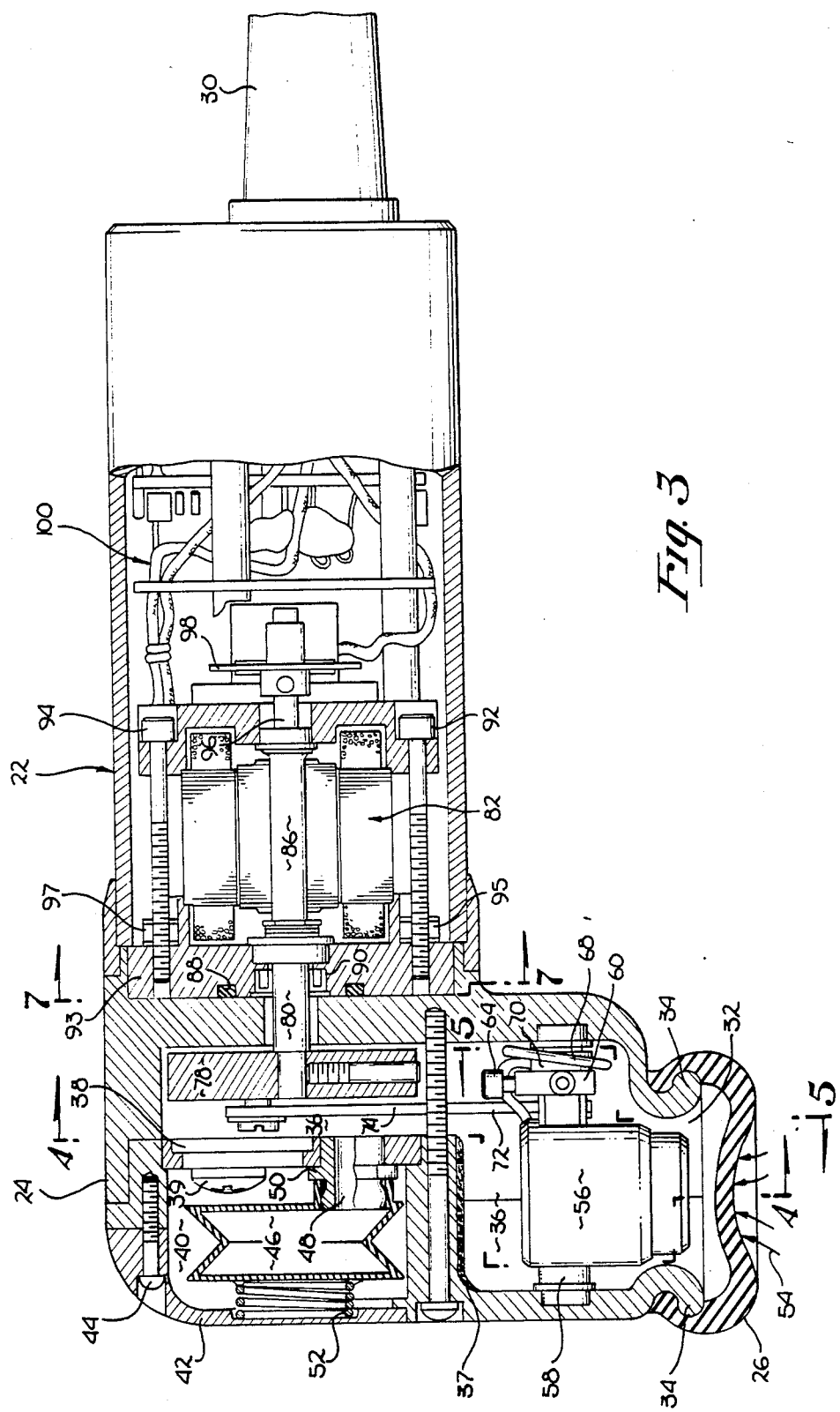

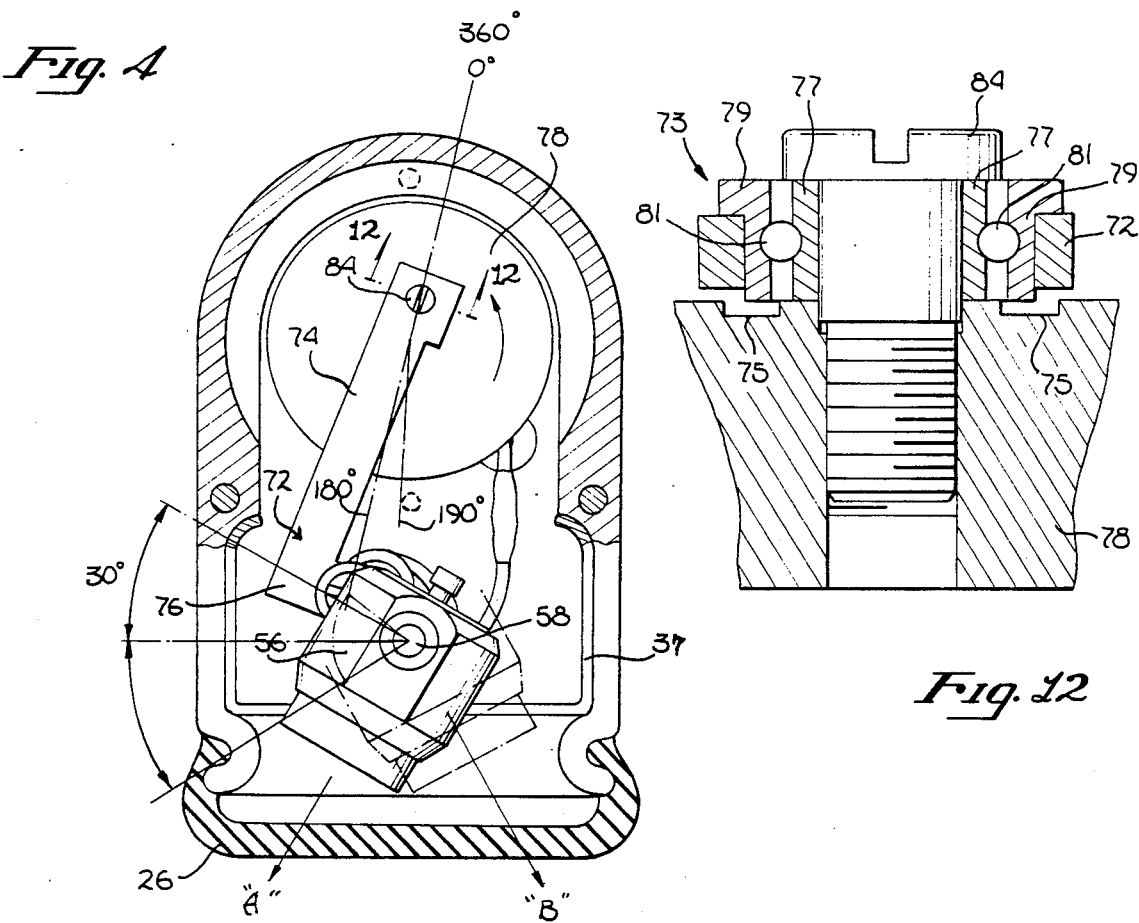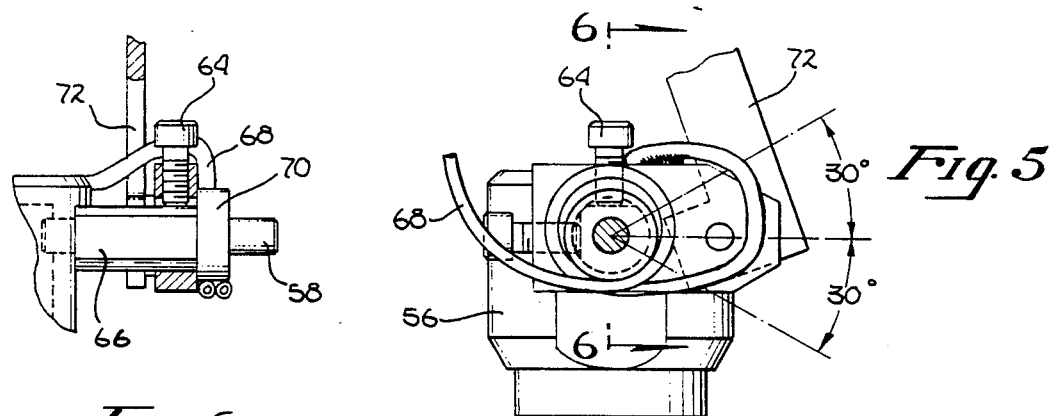

NEONATE ULTRASONIC SCANNER

This is a continuation of application Ser. No. 06/383,562, filed June 1, 1982, now abandoned.

BACKGROUND OF THE INVENTION

1. Field of the Invention

The present invention relates to the field of ultrasonic scanners, and in particular, to ultrasonic scanners used for medical diagnostics.

2. Art Background

Within the past decade, the use of ultrasound for medical diagnostic purposes has found wide application. Unlike prior methods such as X-Ray, surgery or the like, ultrasonic energy as used in medical diagnostics is considered safe. Ultrasonic scanning is frequently used to obtain pictorial cross sections of the body, measuring the performance of the heart and blood flow and for identifying tumors, cysts, and other abnormalities. In addition, ultrasonic scanning has particular application to the examination of pregnant women and infants. In the field of obstetrics, ultrasonic scanning has almost completely supplanted older methods of visualizing the uterus.

In recent years, a variety of ultrasonic scanning systems have been developed (See, for example, U.S. Pat. Nos. 4,149,419 and 4,143,554, as well as co-pending U.S. patent application, Ser. No. 292,948, filed Aug. 14, 1981 which is assigned to the assignee of the present application).

However, when scanning a neonate (an infant less than one month old) or other small child, the ultrasonic scanner must be light, and the interface between the scanning transducer and skin sufficiently pliable, to insure mobility as well as comfort for the patient. In addition, the scanner must be sufficiently compact such that a neonate may be examined, for example through the fontanelle, without the necessity of removal from the intensive care isolette. However, ultrasonic scanners prior to the present invention were generally not designed for neonatal applications, and as a result are typically too cumbersome for use on neonates.

Moreover, most scanners used in the prior art do not incorporate the optimum transducer choice for neonate applications. Inasmuch as high frequency transducers are subject to attenuation with increasing penetration, scanners designed for subjects other than neonates generally use transducers with a frequency of less than 6 Mhz. However, since required penetration is minimal in the case of neonates, higher frequencies with attendent increased resolution may be successfully utilized. Accordingly, there exists a need for an ultrasonic scanner which will provide quality ultrasonic images of neonates and other infants, while maintaining comfort during the examination.

The present invention is designed for use in examining infants, particularly neonates, and incorporates feature not previously found in the prior art to provide improved ultrasonic scans and flexibility while maintaining patient comfort.

SUMMARY OF THE INVENTION

An ultrasonic scanner having particular application to neonate scanning is disclosed. A hand-holdable housing includes an upperr head assembly and a lower drive assembly. The upper head assembly includes a fluid chamber filled with a liquid couplant. An oscillating transducer is mounted on a linkage which is coupled off center to a flywheel within the fluid chamber. A motor disposed within the lower drive assembly rotates the flywheel thereby driving the transducer in an asymmetric oscillatory scanning motion. The placement of the transducer with its associated linkage within the fluid chamber significantly reduces friction, and provides for a smoother rotation of the transducer. A bladder is provided within the upper head assembly which is in fluid communication with the fluid chamber, and normally compressed by a spring. The application of external pressure to the membrane boot of the scanner causes increased fluid pressure within the fluid chamber, thereby expanding the bladder and compressing the spring. Once the external pressure is removed, the spring once again extends and compresses the bladder, thereby forcing fluid outward and maintaining a generally constant fluid pressure within the chamber. Supporting external electronics are provided including means for compensating for the asymmetric motion of the transducer, such that a stable continuous ultrasonic scan is achieved.

BRIEF DESCRIPTION OF THE DRAWINGS

FIG. 1 is a perspective view showing the overall shape of the present invention.

FIG. 2 is a partial cut-away top view of the present invention as shown in FIG. 1.

FIG. 3 is a partial cross-section of the present invention, generally taken through section line 3—3 of FIG. 2.

FIG. 4 is a cross section of the upper head assembly of the present invention, taken along line 4—4 of FIG. 3.

FIG. 5 is a bottom view of the ultrasonic transducer base mount of the present invention taken along line 5—5 of FIG. 3.

FIG. 6 is cross-sectional view of the transducer base mount of the present invention taken along line 6—6 of FIG. 5.

FIG. 11 is a diagramatical illustration of the transducer firing positions and the corresponding RAM look-up table output.

DETAILED DESCRIPTION OF THE INVENTION

Figure 7:
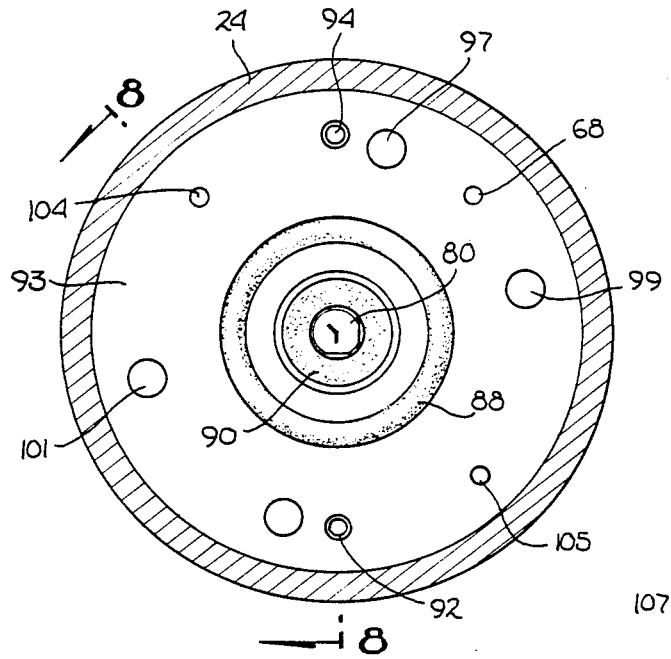
FIG. 7 is a cross-sectional view of the lower drive assembly of the present invention taken along line 7—7 of FIG. 3.

An ultrasonic scanner having particular application to neonate scanning is disclosed. In the following description, numerous details are set forth such as specific frequencies, tolerances, thicknesses, etc., in order to provide a thorough understanding of the present invention. However, it will be obvious to one skilled in the art that the invention may be practiced without these specific details. In other instances, well-known components, structures and electrical processing means have not been described in detail in order not to obscure the present invention unnecessarily.

Referring now to FIGS. 1 and 2, the ultrasonic scanner of the present invention is indicated generally by reference numeral 20. The scanner 20 includes a generally cylindrical lower drive assembly 22 and a upper head assembly 24. As is illustrated, the upper head assembly 24 comprises a two-piece unit to permit easy assembly, both halves of the upper head assembly being secured together by seal screw 25. Thus, the scanner 20 is readily hand-holdable and is generally L-shaped to permit easy entry and mobility within confined areas, such as for example an intensive care isolette. As will be discussed, a soft membrane boot 26 is affixed to the upper head assembly 24, as illustrated, to permit ultrasonic signals to pass from the scanner into the patient's body 28. A cable 30 couples the scanner 20 with an electrical processing unit (not shown) which typically incorporates a cathode ray tube (CRT) in order to display the resulting ultrasonic image.

Referring now to FIG. 3, the upper head assembly 24 includes an open end 32 defined by flanged lips 34. Open end 32 is sealed by a soft flexible membrane boot 26 which permits ultrasound to pass from the scanner into the body which is to be examined. In the presently preferred embodiment, the boot 26 is comprised of SARAN and the thickness is sized such that it is sufficiently pliable to allow the scanner 20 to conform to the contour of a neonate's body.

The upper head assembly 24 includes a fluid chamber 36, one end of the fluid chamber being defined by the membrane boot 26. The fluid chamber 36 is filled with an ultrasonic liquid couplant, such as for example castor oil, as is known in the art, in order to match the acoustic impedance of the liquid to that of the patient's body. Thus, the velocity of ultrasound in the fluid approximately equals the velocity of ultrasound in the body 28. Appropriate seals are provided throughout the head assembly 24 to retain the fluid within the fluid chamber without leakage. Fill ports (see description relative to FIGS. 8 and 9) are used to fill the chamber 36, and portions of the fluid chamber are lined with an acoustic shield 37 in order to reduce ultrasonic reverberations within the fluid chamber. A window 38 is provided to allow the operator to insure that no air bubbles are present in the fluid chamber, inasmuch as the presence of gas bubbles may introduce artifacts into the ultrasonic image. As will be apparent, by appropriately tilting the scanner 20, the operator may view any bubbles which may be present in the chamber 36 through window 38, and remove them by unseating a seal screw 39 positioned adjacent to the window and guiding the bubbles through the screw passage out into the ambient environment.

An air space 40 is disposed within the upper head assembly 24, the upper portion of the air space 40 being defined by a removable lid 42 secured onto the head assembly by screw 44. Air space 40 houses a deformable and inflatable accordian like bladder 46. The bladder 46 is in fluid communication with the fluid chamber 36 through a passage 48 to allow fluid to pass into and out of the fluid chamber and bladder in response to pressure provided on the membrane boot 26, as will be described. A fitting 50 and appropriate sealing means are provided to insure that couplant fluid does not leak into the air space 40. A coil spring 52 is disposed above the bladder 46 and biases the bladder such that it is normally compressed without a significant quantity of couplant fluid being contained within it. Thus, it will be appreciated that in order to view bubbles through window 38 and remove them using screw 39, it is necessary to remove lid 42 and fold bladder 46 over. As illustrated in FIG. 3, upon the application of pressure 54 to the membrane boot 26, fluid within the fluid chamber 36 is forced through the passage 48 and into the bladder 46 thereby expanding it. The expansion of the bladder effectively increases the total volume of the fluid chamber, and thus compensates for the volume loss and resulting increased fluid pressure caused by the inward deformation of the membrane boot 26. The expansion of the bladder compresses the spring 52 toward lid 42. Once the pressure 54 is removed from the boot 26, the spring 52 once again compresses the bladder forcing the fluid back into the fluid chamber 36, thereby maintaining generally equal pressure within the fluid chamber at all times. The present invention's use of a compressible bladder permits the membrane boot 26 to be exceptionally pliable and to conform to the various surface features of the patient's body, while recovering its original shape after each scanning session.

An ultrasonic transducer 56 is mounted on a shaft 58 which is journaled at each end into the upper head assembly 24, for rotation about the shaft's longitudinal axis. As will be described, transducer 56 is oscillated in an asymmetric motion, and in the presently preferred embodiment operates in the frequency range of 6 to 7.5 MHz., with a focal length of approximately 5.4 centimeters. Although a variety of transducers may be used in conjunction with the present invention, it has been found that a transducer incorporating the above specifications provides optimum neonatal ultrasonic images. In addition, the use of compressible bladder 46 allowing the membrane boot to deform, permits transducer 56 to be placed closer to the patient's skin (typically within 5 mm), thereby significantly reducing ultrasonic reverberations and improving image quality. Shaft 58 is rotated within the upper head assembly 24 by a base mount 60 which is rigidly coupled to the shaft 58, by screws 62 and 64. Screws 62 and 64 are disposed generally at 90 degrees with respect to one another through threaded passages (see FIG. 5) within the base mount 60. With reference to FIGS. 3, 5 and 6, base mount 60 includes passage 66 through which the lower portion of shaft 58 passes. Once correctly positioned, screws 62 and 64 are tightened, thereby maintaining the transducer 56 in a fixed relationship with the base mount 60 during operation. As is illustrated, a coaxial 68 extends from the transducer 56 and is coiled around the lower portion 70 of the base mount 60, so as to preclude entanglement of the coaxial cable 68 and relieve strain created by the movement of the transducer.

The transducer 56 is driven in an oscillatory motion by an L-shaped link 72, which includes a strut 74 and an arm 76. The arm 76 is coupled for rotation to the base mount 60, with the strut 74 being coupled off-center to a flywheel 78 which is also disposed within the fluid chamber 36, as best shown in FIGS. 4 and 5. As will be discussed, flywheel 78 is in turn coupled to a flywheel shaft 80 which passes from the upper head assembly 24 into the lower drive assembly 22, which is in turn coupled to an electric motor 82, as illustrated in FIG. 3. In practice, it has been found that the placement of the flywheel 78 with its associated linkage within the fluid chamber 36 significantly reduces friction within the transducer drive system, and provides for a smoother rotation of the transducer.

Referring now to FIG. 4, the mechanism for converting the rotational movement of the flywheel 78 to angular movement of the transducer 56 is illustrated. Strut 74 of link 72 is coupled off-center to the flywheel 78 by screw 84. Unlike conventional lock-spring washer arrangements, the present invention utilizes a hard ball bearing inner race 77 pressed against the soft metal of flywheel 78 to provide a positive locking arrangement.

Figure 12:
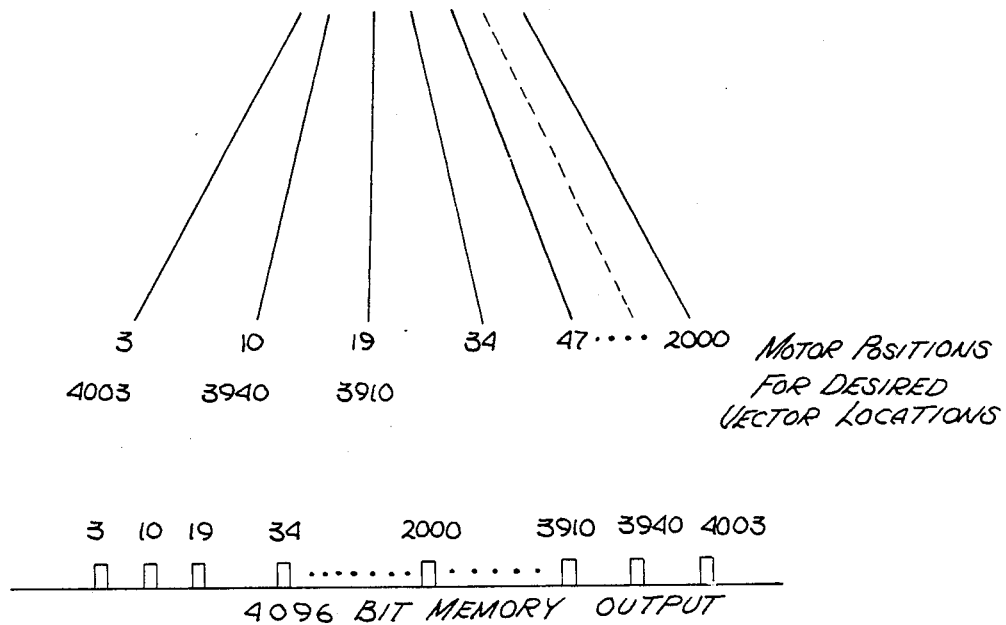
FIG. 12 is a cross-sectional view of the shoulder screw and flywheel taken along line 12—12 of FIG. 4.

As shown in FIG. 12, flywheel 78 is provided with a countersunk circular indentation 75 such that inner race 77 is maintained in a fixed relationship relative to the flywheel 78. However, outer race 79 of the locking bearing 73 lies above indentation 75, so as to permit outer portion 79 and link 72 to freely rotate around screw 84 on ball bearings 81.

As will be appreciated from the figures, the rotation of the flywheel 78 alternately "pushes" and "pulls" the transducer base mount 60 in opposite directions. This movement causes the shaft 58 and the transducer 56 to rotate about the longitudinal axis of the shaft 58 in an oscillatory motion. One flywheel rotation results in a forward and a backward sweep of the transducer (thereby scanning a generally 60 degree arc), which corresponds in operation to two frames of ultrasonic images. In the presently preferred embodiment, the motor 82 is operated at two speeds, such that the transducer provides either 10 or 20 frame/sec. The slower speed being used in cases where higher line density of stationary objects is required. For objects (such as heart valves) which are moving, 20 frames/sec is utilized to provide a real-time image.

It will be apparent that the off-center coupling of the link 72 to flywheel 78 results in an asymmetric oscillation of the transducer 56 about the shaft axis. Specifically, as illustrated in FIG. 4, if position "A" is considered the 0 degree starting position, a flywheel rotation of approximately 190 degrees will swing the transducer from position "A" to position "B", with further rotation of the flywheel from 190 degrees to 360 degrees swinging the transducer from position "B" back to position "A". Thus, inasmuch as motor 82 rotates at one of two substantially constant speeds, the time for the transducer 56 to scan from position "A" to position "B" will not equal the scan time from positon "B" back to position "A". Therefore, absent some means of correction, the asymmetric oscillatory motion of the transducer 56 would result in a flicker in the displayed image on a CRT or the like, inasmuch as the position of the transducer when ultrasonic pulses are emitted during the forward sweep, would not correspond to the transducer position when ultrasonic pulses are emitted during the backward sweep. However, as will be discussed, the present invention incorporates electronic means which correct for this asymmetric motion, and allow the scanner 20 to utilize a single scanning transducer. Unlike scanners in the prior art which require multiple transducers which are difficult to align, the present invention's use of the single transducer significantly simplifies the mechanical design and allows the construction of a more compact neonate scanning unit.

With reference once again to FIG. 3, flywheel shaft 80 of the flywheel 78 passes into the lower drive assembly 22 and forms the central drive shaft 86 of the motor 82. Appropriate seals, such as for example O-ring 88 and bearing seal 90, are provided to preclude fluid leakage from the fluid chamber 36. The upper head assembly 24 is coupled to the lower drive assembly 22 by a base flange 93 which is secured by four screws 95, 97, 99 and 101 (See FIG. 7). Electric motor 82 is mounted within the lower drive assembly by screws 92 and 94, which also assist in coupling the lower drive assembly 22 to the upper head assembly 24. The motor 82 further includes an encoder shaft 96 which is formed as an extension of the central drive shaft 86 for rotating an encoder disc 98. As will be discussed below, the encoder disc 98 includes a plurality of evenly disposed radial slits cut through the disk near its periphery. A photoelectric emitter and detectors are secured on opposite sides of the encoder disk within the assembly 22, to allow the supporting electronics of the present invention to determine the instantaneous position of the transducer 56 as it oscillates. Associated electronics 100, such as preamplifiers and the like are disposed below the motor 82, as illustrated, and are electrically coupled to commonly utilized external data processing electronics through cable 30.

Figure 9:
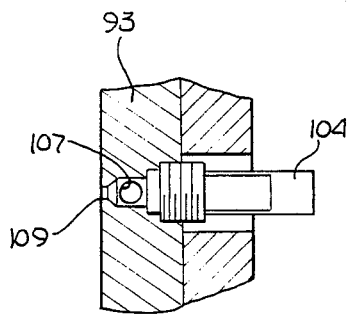
FIG. 9 is a cross-sectional view of the fill port of FIG. 8 taken along line 9—9 of FIG. 8.
Figure 8:
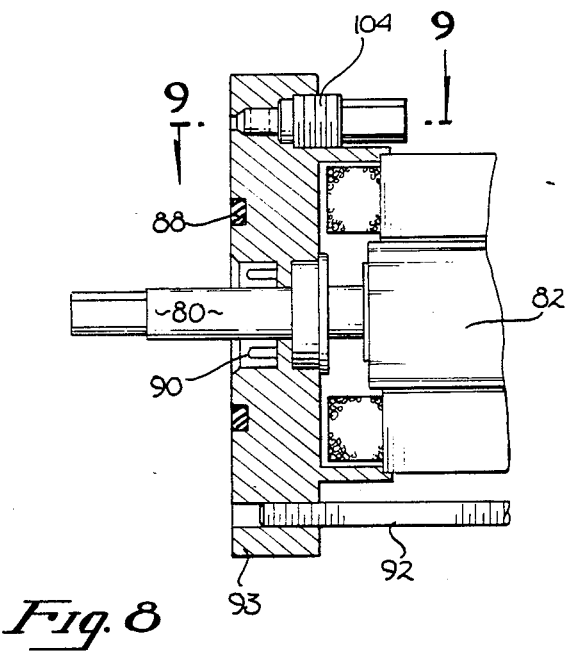
FIG. 8 is a partial cross-sectional view of a fill port within the lower drive assembly taken along line 8—8 of FIG. 7.

Referring now to FIG. 7, a cross-section of the lower drive assembly 22 along line 7—7 of FIG. 3 is illustrated. Transducer coaxial cable 68 passes through the lower wall of the upper head assembly 24 via a male coaxial connector (not shown). The male coaxial connector is aligned with and coupled to a female connector (not shown). The coaxial cable 68 within the lower assembly 22 is then coupled to the associated electronics 100 of the lower drive assembly. Fill ports 104 and 105 are provided to permit the operator to fill the fluid chamber 36 after the upper assembly 24 has been mounted onto the lower drive assembly 22. In the presently preferred embodiment, the fill ports are disposed in an approximate 45 degree angle relative to the motor mount screws 92 and 94 as illustrated in FIG. 8. Prior to the installation of the outer cylindrical cover of the lower drive assembly, couplant fluid may be inserted through fill ports 104 and 105 in order to fill the fluid chamber 36. As best shown in FIG. 9, in order to inject fluid through the port, the operator unscrews ports 104 and 105 to permit fluid to pass from the valve through orifice 107 of the port and into the passage 109 leading to chamber 36. When filling is complete, the user simply tightens the port thereby sealing the passage and preventing leakage.

Figure 10:
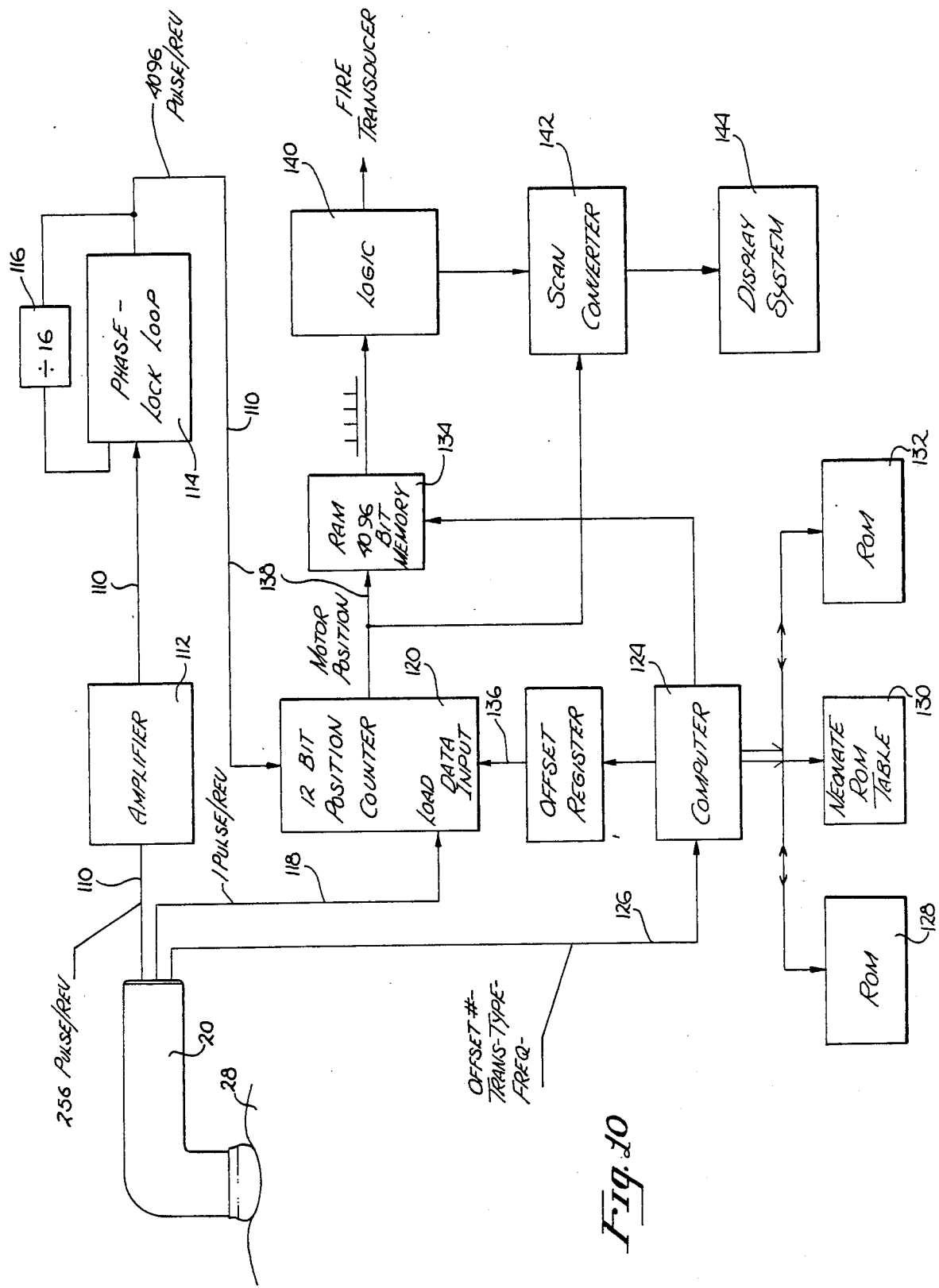
FIG. 10 is a block diagram of the external circuitry utilized by the present invention to correct for the asymmetric motion of the ultrasonic transducer.

Referring now to FIG. 10, the electronic processing means employed by the present invention to correct for the asymmetric motion of the transducer will be described. Well known circuit means are used to process the electrical signals from the transducer 56 in order to provide the various ultrasonic scans commonly used in the art. Display circuitry and signal processing techniques for ultrasound displays are described in U.S. Pat. No. 4,241,412. As previously discussed, encoder disc 98 is coupled for rotation to electric motor 92. In the presently preferred embodiment, encoder disc 98 includes 256 slits equally spaced and extending radially from the center thereof. Since for any given motor speed the motor 82 rotates at a substantially constant rate, the output of the photo-detectors comprise 256 pulses per motor revolution. This output is coupled to line 110 and passes through amplifier 112 for amplification. The signal pulses are then coupled to a phase lock loop 114 and a divide by 16 counter 116 to provide 4,096 pulses per motor revolution on the line 110.

In addition to the 256 pulse/revolution output, scanner 20 also outputs from the photo-emitter and detector combination a 1 pulse per motor revolution reset signal on line 118. As illustrated, lines 110 and 118 are coupled to a 12 bit position counter 120, with the 1 pulse per revolution reset signal line 118 being coupled to the "load" port of the counter 120. In addition, during the manufacture of each individual scanner 20, each scanner is provided with a read only memory (ROM) which is programmed with codes corresponding to the type of transducer utilized by the particular scanning unit, the frequency of the particular transducer included within the scanning unit, and a unique offset number indicating any mechanical variance between the particular scanner and the engineering design specifications. This data is coupled to a computer 124 (typically a microprocessor) on line 126. For simplicity, numerous other lines comprising cable 30 of scanner 20 (such as for example transducer data lines and control lines etc.) are not shown in order not to obscure the present invention unnecessarily. However, it will be apparent to one skilled in the art that these well known additional lines are required for operation of the device.

In operation, codes within the scanner ROM are read by computer 124 during the initial start-up procedures of the ultrasound system. Computer 124 is typically coupled to a variety of ROMS such as 128, 130 and 132 which contain tables corresponding to the positions at which the transducers used by a variety of scanners are to be fired. Based on the type of scanner utilized, as indicated by the coded data provided to the computer from the particular scanner ROM, computer 124 loads the appropriate firing table for the present invention into a 4,096 bit random access memory (RAM) 134, which is coupled both to the computer 124 as well as the 12 bit position counter 120. In addition, the offset number for the particular scanner being used is provided to the position counter on line 136 in order to calibrate the electronic system to the individual mechanical characteristics of the scanner being used.

Assume for sake of example that the calibration pulse is received by the position counter on line 118. The counter is then reset indicating that the transducer is at a current startup position. As pulses are received on line 110, the counter is incremented and outputs a current motor position on line 138. As best illustrated in FIG. 11, the position of the transducer along each forward and backward sweep is divided into 4,096 finite increments. Thus, despite the difference in the time required per sweep due to the asymmetric motion of the transducer 56, each desired firing position of the transducer corresponds to two incremental locations, one for the forward sweep, and the other for the backward sweep. For example, an ultrasonic pulse which is to be emitted at motor position 10 on the forward sweep corresponds to position 3940 during the backward sweep, such that an ultrasonic pulse is emitted at substantially the same transducer position during each asymmetric oscillation. It will be appreciated to one skilled in the art that if the transducer was simply fired at equal time intervals during each rotation of the motor 82, that a flicker of the image would result inasmuch as the asymmetric motion of the transducer would result in the transducer being fired at different positions during each forward and backward sweep.

Referring once again to FIG. 10, each motor position which is coupled to line 138 corresponds to an address within the 4,096 bit RAM 134 which acts as a look-up table. Thus, (as best shown in FIG. 11) for predetermined firing positions, the output signal state of the RAM 134 is altered at each motor position where transducer firing is to occur. Logic unit 140 issues the appropriate commands to fire the transducer 56 within the scanner 20 upon sensing the appropriate state change from the RAM 134.

In addition, motor position line 138 is also coupled to a scan converter 142 which in turn is coupled to a display system 144 for displaying the resultant ultrasonic image provided by the scanner 20. Inasmuch as the generation of ultrasonic images from received transducer pulses is well known in the art, a detailed description of the scan converter and display system will not be set forth herein. Moreover, it will be appreciated that although the present invention utilizes a 4,096 increment system, that a variety of discrete positions may be employed in order to correct for the asymmetric motion of the transducer.

Thus, an improved ultrasonic scanner having particular application to neonatal scanning has been disclosed. While the scanner has been particularly described with reference to FIGS. 1-12 and with emphasis on neonatal scanning, it should be understood that the figures are for illustration and should not be taken as limitations upon the invention. It is contemplated that many changes and modifications may be made, by one of ordinary skill in the art, to the materials and arrangements of elements of the invention without departing from the spirit and scope of the invention as disclosed above.

We claim:

1. An ultrasonic scanner comprising:
   a hand-holdable housing including an upper head assembly and a lower drive assembly;
   a fluid chamber within said upper head assembly, including a membrane defining a portion of said chamber for contacting a body;
   a fluid disposed within said fluid chamber;
   an ultrasonic transducer within said fluid chamber mounted for pivotal movement about an axis, such that ultrasound from said transducer passes through said membrane into said body;
   drive means for pivoting said transducer about said axis in an asymmetric oscillatory motion, such that the time required for said transducer to sweep in one direction is different than the time required for said transducer to pivot in the opposite direction, said drive means including:
   a flywheel disposed within said fluid chamber;
   a motor coupled to said flywheel, for rotating said flywheel at a substantially constant motor speed;
   linkage means disposed within said fluid chamber, including a link coupled off-center to said flywheel and to said transducer, for asymmetrically oscillating said transducer about said axis.

2. The scanner as defined by claim 1, further including encoder means coupled to said motor for dividing oscillations of said transducer into finite increments, such that the position of said transducer may be determined at any given time.

3. The scanner as defined by claim 2, further including electronic processing means coupled to said encoder means for compensating for the asymetric motion of said transducer, such that an ultrasonic pulse is emitted by said transducer at substantially the same position during each oscillatory sweep of said transducer.

4. The scanner as defined by claim 3, wherein said electronic processing means further includes look-up table memory means coupled to said encoder means to provide a signal to trigger the emission of an ultrasonic pulse from said transducer when said transducer is at predetermined positions.

5. The scanner as defined by claim 4, wherein said linkage means includes an "L"-shaped link having an arm and a strut, said arm being coupled to said transducer, and said strut being coupled off-center to said flywheel.

6. The scanner as defined by claim 5, wherein said strut is coupled to said flywheel by a locking bearing having an inner and outer engagement portion, said outer portion disposed above the surface of said flywheel and said inner portion pressed into engagement with said flywheel by a screw, whereby said outer portion and linkage means are free to rotate around said inner portion and screw.

7. The scanner as defined by claim 6, wherein said transducer emits ultrasonic pulses in the frequency range of 6 to 7.5 MHz.

* * * * *

UNITED STATES PATENT AND TRADEMARK OFFICE
CERTIFICATE OF CORRECTION

PATENT NO. : 4,517,985
DATED : May 21, 1985
INVENTOR(S) : Teslawski et al,

It is certified that error appears in the above-identified patent and that said Letters Patent is hereby corrected as shown below:

| COLUMN | LINE | DESCRIPTION |
|--------|------|-------------|
| 4 | 49 | Please delete "coaxial 68" and insert --coaxial cable 68--. |

Signed and Sealed this

Twenty-fourth Day of February, 1987

Attest:

DONALD J. QUIGG

Attesting Officer      Commissioner of Patents and Trademarks